(12) United States Patent
Hu et al.

(10) Patent No.: US 11,116,659 B2
(45) Date of Patent: Sep. 14, 2021

(54) BODY TEMPERATURE MANAGEMENT DEVICES AND METHODS

(71) Applicant: UNIVERSITY OF MARYLAND, BALTIMORE, Baltimore, MD (US)

(72) Inventors: Bingren Hu, Baltimore, MD (US); Chunli Liu, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 785 days.

(21) Appl. No.: 15/746,826

(22) PCT Filed: Jul. 27, 2016

(86) PCT No.: PCT/US2016/044180
§ 371 (c)(1),
(2) Date: Jan. 23, 2018

(87) PCT Pub. No.: WO2017/019730
PCT Pub. Date: Feb. 2, 2017

(65) Prior Publication Data
US 2018/0207028 A1    Jul. 26, 2018

Related U.S. Application Data

(60) Provisional application No. 62/197,116, filed on Jul. 27, 2015.

(51) Int. Cl.
*A61F 7/12* (2006.01)
*A61F 7/00* (2006.01)
(Continued)

(52) U.S. Cl.
CPC ............. *A61F 7/12* (2013.01); *A61F 7/0085* (2013.01); *A61F 7/123* (2013.01);
(Continued)

(58) Field of Classification Search
CPC .............. A61B 5/6853; A61B 1/00082; A61B 2017/22051–22071; A61F 7/123; A61F 7/12; A61F 2/2433; A61F 2007/126
See application file for complete search history.

(56) References Cited

U.S. PATENT DOCUMENTS 5,151,100 A    9/1992 Abele et al.
5,158,536 A *  10/1992 Sekins .............. A61M 16/0479
                                              604/20
(Continued)

FOREIGN PATENT DOCUMENTS

CN    202397589    2/2012
WO    2012/139980  10/2012
(Continued)

OTHER PUBLICATIONS

International Search Report issued corresponding International Application No. PCT/US16/44180 dated Oct. 28, 2016.
(Continued)

*Primary Examiner* — Linda C Dvorak
*Assistant Examiner* — Annabeth E Rodriguez
(74) *Attorney, Agent, or Firm* — Whiteford, Taylor & Preston, LLP; Gregory M. Stone

(57) ABSTRACT

Disclosed are devices and methods for body temperature management using a heat transfer catheter carrying a heat transfer fluid to heat or cool a desired, focused portion of a patient's body. In accordance with certain aspects of the invention, the heat transfer catheter may include hollow nodes that have greater rigidity than the remainder of the catheter to aid in placement of the heat transfer catheter within and navigation of the desired portion of the patient's body. Methods of using such heat transfer catheter to effect temperature management of the patient's body are also disclosed.

16 Claims, 3 Drawing Sheets

(51) Int. Cl.
*A61F 7/02* (2006.01)
*A61B 18/00* (2006.01)
*A61B 90/00* (2016.01)
*A61F 7/03* (2006.01)

(52) U.S. Cl.
CPC ............... *A61B 2018/00714* (2013.01); *A61B 2018/00791* (2013.01); *A61B 2018/00982* (2013.01); *A61B 2090/064* (2016.02); *A61B 2217/005* (2013.01); *A61B 2217/007* (2013.01); *A61B 2218/002* (2013.01); *A61B 2218/007* (2013.01); *A61F 7/034* (2013.01); *A61F 2007/0028* (2013.01); *A61F 2007/0054* (2013.01); *A61F 2007/0096* (2013.01); *A61F 2007/0276* (2013.01); *A61F 2007/126* (2013.01)

(56) References Cited

U.S. PATENT DOCUMENTS

| | | | |
|---|---|---|---|
| 5,938,623 A | 8/1999 | Quiachon et al. | |
| 5,993,377 A | 11/1999 | Hartwig | |
| 6,440,158 B1 | 8/2002 | Saab | |
| 6,641,602 B2 | 11/2003 | Balding | |
| 6,716,236 B1* | 4/2004 | Tzeng | A61F 7/12 607/105 |
| 7,758,623 B2* | 7/2010 | Dzeng | A61F 7/123 607/105 |
| 8,231,664 B2 | 7/2012 | Kulstad et al. | |
| 8,888,729 B2 | 11/2014 | Noda et al. | |
| 2002/0111584 A1 | 8/2002 | Walker et al. | |
| 2002/0120314 A1* | 8/2002 | Evans | A61F 7/12 607/96 |
| 2002/0151943 A1* | 10/2002 | Balding | A61F 7/123 607/105 |
| 2003/0040782 A1 | 2/2003 | Walker et al. | |
| 2004/0133256 A1* | 7/2004 | Callister | A61F 7/123 607/105 |
| 2007/0239192 A1 | 10/2007 | Litzenberg et al. | |
| 2010/0049184 A1 | 2/2010 | George et al. | |
| 2010/0087781 A1 | 4/2010 | Adams et al. | |
| 2012/0265188 A1 | 10/2012 | Buchbinder et al. | |
| 2013/0296985 A1 | 11/2013 | Noda et al. | |
| 2015/0045781 A1 | 2/2015 | Abboud et al. | |
| 2015/0141898 A1 | 5/2015 | Cattaneo | |

FOREIGN PATENT DOCUMENTS

| | | |
|---|---|---|
| WO | 2013/164820 | 11/2013 |
| WO | 2017/019730 | 2/2017 |

OTHER PUBLICATIONS

Supplementary European Search Report issued in corresponding European Patent Application No. 16831266 dated Mar. 8, 2019.

* cited by examiner

BODY TEMPERATURE MANAGEMENT DEVICES AND METHODS

CROSS REFERENCE TO RELATED APPLICATIONS

This application is based upon and claims priority from U.S. Provisional Patent Application No. 62/197,116, titled "Colon-Rectum Temperature Management Devices and Methods" and filed on Jul. 27, 2015 by the inventors herein, which is hereby incorporated by reference for all purposes as if fully set forth herein.

FIELD OF THE INVENTION

The present invention relates generally to the field of medicine, and more particularly to a method and apparatus for controlling and managing the temperature of humans and animals.

BACKGROUND

The medical community has come to accept that induced therapeutic hypothermia may be used to achieve cardio-protection and neuro-protection. Currently there is sufficient evidence to regard therapeutic hypothermia as standard of care for situations such as patients with postanoxic encephalopathy. Further, therapeutic hypothermia has shown promising results in the treatment of head injury, stroke, subarachnoid hemorrhage (SAH), and in other situations. During emergency care and during surgery, inducing the hypothermic state may help to reduce local and systemic inflammation, tissue swelling, blood loss, and other adverse bodily reactions to hypoxia, ischemia, trauma, and surgical procedures. Medical professionals expect that other therapeutic benefits of inducing hypothermia to regulate body temperature will be discovered according to further development in this field.

There is still a need for more work and study to be done in order to identify the specific clinical situations in which hypothermia can be effective. However, many medical professionals have shifted their focus from assessment of clinical efficacy studies to finding ways to technically implement induced therapeutic hypothermia.

Currently there are three well known and used cooling techniques and systems: conventional cooling systems; surface cooling systems; and intravascular cooling systems. In addition to these cooling techniques, in recent years, a number of medical professionals and scientists have proposed cooling techniques via colo-rectal heat exchangers. For example, U.S. Pat. No. 6,641,602, by David P. Balding, the specification of which is incorporated herein by reference in its entirety, discloses a "Method and device including a colo-rectal heat exchanger." The device disclosed in this patent includes a balloon-type heat exchange tube, which is used to regulate the temperature of a patient by inserting the heat exchange tube into the colon of the patient. The temperature of the heat exchange tube can be adjusted and/or controlled by running a cooling fluid through the tube. The heat exchange tube is inflated with a heat exchange fluid flowing into the tube from a temperature control unit. The fluid remains inside the tube and is not infused into the patient. The heat exchange tube includes therein an inflow lumen, an outflow lumen, and an irrigation lumen for irrigating the colon.

The cooling technique presented in U.S. Pat. No. 6,641,602 has several advantages with respect to currently used cooling techniques, such as avoiding the risk of infections and thrombosis associated with the use of intra vascular devices where a solution is inserted into the blood stream resulting in change in a patient's fluid balance. Moreover, the inside of the patient's body can be heated and/or cooled at a rapid rate due to the large surface area within the colon.

The human colon (and the colon of other animals) includes various turns. FIG. 1 shows schematically the four regions of the human colon: the sigmoid colon, the ascending colon, the transverse colon and the descending colon. These regions are separated by at least four turns (labeled 1-4 in FIG. 1). As a result, a heat exchanger device needs to be able to be moved/slide along the colon such as to advance over the turns in the colon. While the tube of the device disclosed by Balding's invention has at least one flex zone to promote bending of the device to allow for conformance of the device to the intestinal anatomy of the patient, it is believed that the highly flexible construction of the outer balloon of the Balding device would render it quite difficult to move and ultimately properly place the heat exchange tube at a desired position within the patient's colon.

Body cooling devices and methods have particular application to those situations in which a reduction of blood supply to human body organs may lead to fatal ischemic injury, as may occur in many military and clinical settings including stroke, heart attack, traumatic hemorrhage, cardiac arrest, organ transplantation, and aorta aneurysm rupture. For example, traumatic hemorrhagic shock alone is responsible for over 35% of pre-hospital deaths. While extremity wounds are more amenable to compression to stop bleeding, 15% of Operation Iraqi Freedom and Operation Enduring Freedom battle injuries were to the torso (chest, abdomen, pelvis and back), where compression cannot be applied. Non-compressible torso hemorrhage (NCTH) is the leading cause of potentially survivable deaths of American troops. The control of bleeding is the only way to avoid the problems associated with massive hemorrhage in trauma. Resuscitative endovascular balloon occlusion of the aorta (REBOA) is a temporary maneuver for stopping NCTH. This technique involves inserting a balloon catheter to the appropriate section of the aorta, and inflating the balloon to occlude blood flow to the lower body, thus stopping the hemorrhage. As a side effect, a "prolonged" usage of REBOA leads to fatal abdominal organ ischemic injury. Similarly, fatal abdominal organ ischemic injury occurs in many other clinical settings including cardiac arrest, organ transplantation, and aorta aneurysm rupture. Currently, there is no active intervention for the prevention of fatal abdominal organ ischemic damage.

Recent studies show that in abdominal organs, such as the intestines and spleen, inflammatory response can lead to local and distant tissue or organ damage, known as systemic inflammatory response syndrome (SIRS). SIRS can occur either due to abdominal organ damage, damage to distant organs such as the brain, sepsis, severe sepsis, septic shock, and multiple organ dysfunction syndrome (MODS). SIRS can also lead to acute respiratory distress syndrome (ARDS).

Hypothermia (HT) is the most effective strategy currently known for ischemic organ protection. Its mechanism of action involves upregulating cell survival while inhibiting inflammatory and cell death activities. Use of deep cooling at 4° C. together with organ-preservation solutions can protect the transplantation organ from ex vivo "ischemic injury" for up to 24-36 hours. Whole body deep cooling to 10-15° C. in large animal models can offer optimal protection from lethal hemorrhagic shock (HS). In aggregate, the current literature agrees that optimized hypothermia is the best strategy to preserve organs from otherwise "irreversible" ischemic injury. In 2007, the FDA approved the first device specifically designed to ameliorate perinatal hypoxic ischemic brain damage. However, there are several challenges for implementing therapeutic hypothermia for adult organ ischemic patients: (i) cooling must be initiated as rapidly as possible for obtaining maximum protection, which is difficult to achieve in humans because even with an invasive endovascular device, cooling a human body even to 33° C. can take more than 1 hour; and (ii) whole body HT is often associated with myocardial dysfunction, pneumonia, and shivering, so that its role in traumatic hemorrhagic shock patients remains controversial.

The above information disclosed in this background section is only for enhancement of understanding of the background of the invention and therefore it may contain information that does not form any part of the prior art.

SUMMARY OF THE INVENTION

Disclosed herein are devices and methods configured to address one or more of the above described disadvantages of the prior art. However, achieving the above purposes and/or benefits is not a necessary feature to each of the exemplary embodiments, and the claims herein may recite subject matter that does not achieve the above stated purpose.

Body temperature management devices and methods are disclosed including a heat transfer fluid carrier that may be positioned within a patient's body to effect heat transfer with the patient's body. For example, such devices and methods may be used to provide Focal Abdominal Cavity Cooling (FACC) to mitigate organ ischemic injury. Studies undertaken by the inventors herein in the rat model of hemorrhagic shock indicate that devices configured in accordance with at least certain aspects of the embodiments set forth herein dramatically reduce mortality as well as lethal organ damage after hemorrhagic shock, and thus provide enough time for the treatment of or for transporting patients to trauma facilities. The devices and methods described herein offer unique advantages, including one or more of the following: (i) the devices and methods set forth herein are non-invasive, portable, and can be easily deployed by non-specialized personnel to induce profound FACC rapidly; (ii) in combination use with REBOA, the devices and methods set forth herein can keep adequate warm circulation to the brain and heart; and (iii) FACC preserves abdominal organs from ischemic injury.

In accordance with certain aspects of an embodiment of the invention, a heat transfer catheter system is provided comprising a heat transfer catheter, the heat transfer catheter further comprising: a plurality of hollow nodes; a flexible conduit attaching adjacent hollow nodes and allowing fluid communication between the adjacent hollow nodes and the flexible conduit, wherein the flexible conduit has greater flexibility than the hollow nodes, and wherein an interior of the hollow nodes and an interior of the flexible conduit provide a heat transfer fluid carrier; and a heat transfer fluid within the heat transfer fluid carrier.

In accordance with further aspects of an embodiment of the invention, a heat transfer catheter system is provided comprising a heat transfer catheter, the heat transfer catheter further comprising: a flexible, cylindrical balloon; an elongate, hollow, cylindrical tube having greater rigidity than the balloon and extending into the balloon from a proximal end of the balloon, and terminating adjacent an internal distal end of the balloon, the tube having a tube distal end opening to an interior of the balloon; a heat transfer fluid inlet line attached to a proximal end of the cylindrical tube; a heat transfer fluid outlet line attached to a proximal end of the balloon; and a heat transfer fluid within the heat transfer fluid carrier.

In accordance with still further aspects of an embodiment of the invention, a method is provided for colo-rectal temperature management, comprising: providing a heat transfer catheter, the heat transfer catheter further comprising: a plurality of hollow nodes; and a flexible conduit attaching adjacent hollow nodes and allowing fluid communication between the adjacent hollow nodes and the flexible conduit, wherein the flexible conduit has greater flexibility than the hollow nodes, and wherein an interior of the hollow nodes and an interior of the flexible conduit provide a heat transfer fluid carrier; inserting the heat transfer catheter into the rectum and colon of a patient; and causing a heat transfer fluid in said heat transfer fluid carrier to effect heat transfer between said heat transfer fluid carrier and the patient's colon.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

DETAILED DESCRIPTION

Figure 1:
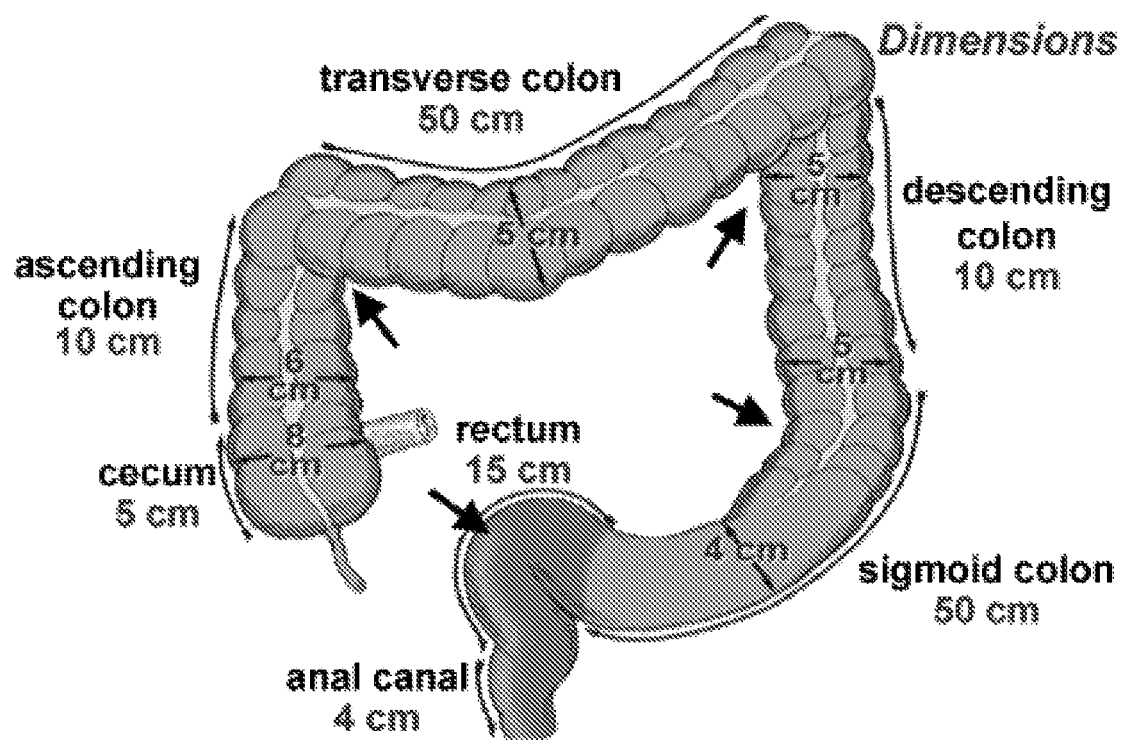
FIG. 1 shows a schematic view of a colon of a human subject.

The following detailed description is provided to gain a comprehensive understanding of the methods, apparatuses and/or systems described herein. Various changes, modifications, and equivalents of the systems, apparatuses and/or methods described herein will suggest themselves to those of ordinary skill in the art. Descriptions of well-known functions and structures are omitted to enhance clarity and conciseness.

Hereinafter, an apparatus and method for performing temperature management of a subject's body is disclosed, and more particularly (with regard to a particular exemplary embodiment thereof) colo-rectal cooling. Embodiments of the invention may, however, be configured in many different forms for various other body temperature management uses and should not be construed as limited to the exemplary embodiments set forth herein. Rather, these exemplary embodiments are provided so that this disclosure is thorough, and will fully convey the scope of the invention to those skilled in the art.

Throughout the drawings and the detailed description, unless otherwise described, the same drawing reference numerals are understood to refer to the same elements, features, and structures. The relative size and depiction of these elements may be exaggerated for clarity. It will be understood that for the purposes of this disclosure, "at least one of X, Y, and Z" can be construed as X only, Y only, Z only, or any combination of two or more items X, Y, and Z (e.g., XYZ, XZ, XYY, YZ, ZZ). Further, it will be understood that when an element is referred to as being "connected to" another element, it can be directly connected to the other element, or intervening elements may be present.

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced item.

The use of the terms "first", "second", and the like does not imply any particular order, but they are included to identify individual elements. Moreover, the use of the terms first, second, etc. does not denote any order or importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Although some features may be described with respect to individual exemplary embodiments, aspects need not be limited thereto such that features from one or more exemplary embodiments may be combinable with other features from one or more exemplary embodiments.

This specification discloses devices and methods for controlling the temperature of a patient or an animal via, in accordance with certain aspects of an embodiment of the invention, a body temperature management device, such as a colon-rectal temperature management device. The devices and methods disclosed herein can be used for the therapy of hemorrhagic and septic shock, trauma, or ischemia-reperfusion injury.

Figure 2:
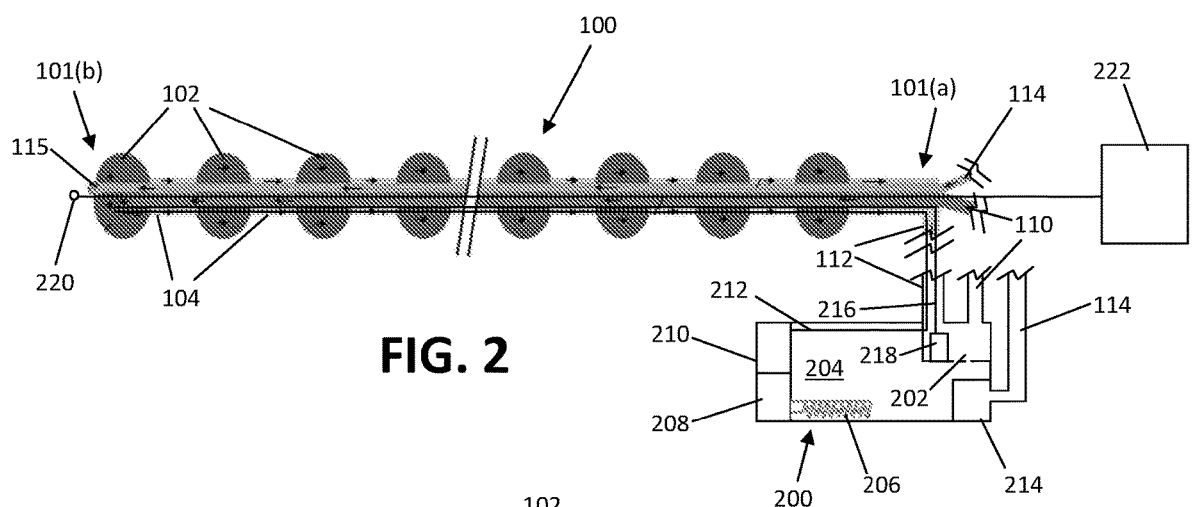
FIG. 2 shows a cross-sectional view of a heat transfer catheter system in accordance with certain aspects of an embodiment of the invention.

FIG. 2 shows a heat transfer catheter system in accordance with certain aspects of an embodiment of the invention, including a heat transfer catheter (shown generally at 100) in fluid communication with a heat transfer fluid control unit (shown generally at 200). In accordance with a particular embodiment, heat transfer catheter 100 is formed as a colo-rectal temperature management catheter for use in a subject's body, and defines a heat transfer fluid carrier that transfers heat between a fluid within heat transfer catheter 100 and such portion of a patient's body in which heat transfer catheter 100 is placed, with such heat transfer being carried out through an outer surface of heat transfer catheter 100. Heat transfer catheter 100 includes a plurality of preferably oval-shaped, hollow nodes 102, and sections of flexible conduit 104 positioned between adjacent pairs of hollow nodes 102, which flexible conduit 104 allows fluid flow between and among nodes 102. In accordance with certain aspects of a particular embodiment of the invention, heat transfer catheter 100 may include a heat transfer fluid inlet line 110 that receives heat transfer fluid from fluid control unit 200, and a heat transfer fluid outlet line 112 that returns heat transfer fluid to fluid control unit 200 in a closed fluid circuit. In this configuration, heat transfer fluid flows into heat transfer catheter 100 from a proximal end 101(a), and flows toward distal end 101(b) of heat transfer catheter 100. At the distal end of heat transfer fluid inlet line 110, heat transfer fluid flows into and fills the interior of heat transfer catheter 100, allowing heat transfer to take place between the outer surface of heat transfer catheter 100 and a patient's body in which heat transfer catheter 100 is placed. The heat transfer fluid then continues to flow from the distal end of heat transfer catheter 100 to the proximal end thereof, until it exits at the proximal end through heat transfer fluid outlet line 112 for return to fluid control unit 200.

Preferably, an irrigation line 114 is also provided and extends from the proximal end of heat transfer catheter 100, through its entire length and to the distal end of heat transfer catheter 100, providing a fluidly isolated channel that may carry irrigation fluid, medication, or other materials through heat transfer catheter 100 for delivery to the patient's body, such as irrigation fluid to clean the patient's colon so as to improve heat transfer between the colon and heat transfer catheter 100.

Heat transfer fluid inlet line 110, heat transfer fluid outlet line 112, and irrigation line 114 may be formed of flexible or elastic materials typically used in catheters and known to those skilled in the art, such as latex, silicone, TEFLON, or the like. Likewise, heat transfer fluid inlet line 110, heat transfer fluid outlet line 112, and irrigation line 114 all connect to their respective connections on fluid control unit 200. With continuing reference to FIG. 2, fluid control unit 200 includes a pump 202 that pumps heat transfer fluid from a chamber 204, into heat transfer fluid inlet line 110 which carries the heat transfer fluid through the length of heat transfer catheter 100 from its proximal end 101(a) to its distal end 101(b), and then back through the interior of heat transfer catheter 100 until it exits through heat transfer fluid outlet line 112, and back into pump 202, all in a closed fluid circuit. Chamber 204 may include a heat exchange element 206 and a temperature regulator 208 of standard configuration and capable of controlling the temperature of heat transfer fluid that is delivered to heat transfer catheter 100. The temperature regulator 208 may, by way of non-limiting example, comprise a container with cold or hot fluid, a compressor device, an exothermic or endothermic device, a Peltier cooling device, a heating device, or a combination of the above.

Preferably, a processor 210 is also provided for maintaining temperature set-points for the heat transfer fluid and for controlling temperature regulator 208. A temperature probe 212 may extend through heat transfer catheter 100 and may communicate with processor 210 to ensure that the temperature of heat transfer fluid within heat transfer catheter 100 is maintained at an intended temperature, and so as to allow processor 210 to control temperature regulator 208 to maintain such temperatures within the established temperature set points. Such temperature probe 212 and regulator 208 are configured to closely control and maintain an accurate fluid temperature of heat transfer fluid within the patient's body in order to reduce the risk of cold or heat damage to the contacted tissue. Due to heat exchange between the heat exchange catheter 100 and the patient's body, the temperature of the circulating heat transfer fluid is significantly different between the inside and outside of the patient's body, and thus should be accurately controlled so that the fluid can perform accurate temperature exchange. For example, when using heat transfer catheter 100 as a rectal colon heat exchanger, the fluid in the intra-rectal colon segment of the device should be maintained at a temperature that is neither too hot nor too cold, thus avoiding the risk of heat or cold damage to the contacted colon tissue.

Further, a pressure sensor 216 may extend through heat transfer catheter 100 and may communicate with a pressure feedback controller 218 having stored thereon established pressure set points (that may be a part or function of processor 210 or separate therefrom) to ensure that the pressure within heat transfer catheter 100 does not exceed a predetermined threshold pressure that might cause rupture of the exterior of heat transfer catheter 100, which rupture could cause damage to the patient's tissue contacting heat transfer catheter 100.

Additionally, fluid control unit 200 may include irrigation unit 214 configured to store and pump irrigation fluid through irrigation line 114 as discussed above. While shown in FIG. 2 as physically attached to the remainder of fluid control unit 200, those skilled in the art will recognize that irrigation unit 214 may likewise be provided as a separate unit therefrom.

Those skilled in the art will recognize that the schematic view of fluid control unit 200 shown in FIG. 2 is exemplary only, and that any mechanisms for pumping and controlling the temperature of a heat exchange fluid to heat transfer catheter 100, and likewise for delivering irrigation fluid through heat transfer catheter 100, may be used without departing from the spirit and scope of the invention. For example, fluid driving devices other than those described above, including by way of non-limiting example a syringe, may be used to deliver heat transfer fluid and/or irrigation fluid to and through heat transfer catheter 100 without departing from the spirit and scope of the invention.

Figure 3:
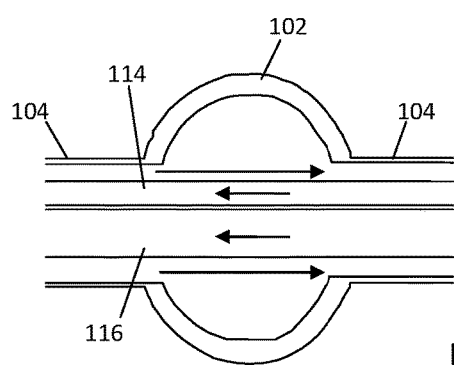
FIG. 3 shows a close-up, cross-sectional view of a portion of the heat transfer catheter system of FIG. 2.

As mentioned above, in accordance with certain aspects of an embodiment of the invention and with reference to the close-up cross-sectional view of FIG. 3, heat transfer catheter 100 includes oval shaped, hollow nodes 102, and sections of flexible fluid conduit 104 positioned between adjacent nodes 102 and allowing fluid communication between and among them. Importantly, nodes 102 are configured with greater rigidity and less flexibility than fluid conduit sections 104. More particularly, while sections of flexible conduit 104 between adjacent nodes 102 may compress during insertion into a patient's body, such as into the patient's colon, it is important that the heat transfer catheter 100 be able to maintain its overall elongate shape during such insertion to allow it to be pushed into the intended location in the patient's body without curling, pinching, or the like. It is also important, however, to ensure that heat transfer catheter 100 be able to bend as it traverses the patient's anatomy, such as their colon. Providing nodes 102 with greater rigidity than the other elements of heat transfer catheter 100 achieves, at least in part, these results. Specifically, nodes 102 are provided sufficient rigidity (and specifically greater rigidity than intermediate sections of flexible conduit 104) so as to not compress during insertion into the patient's body, such as their colon, and instead each node 102 will serve to push an adjacent node further into the patient's colon during insertion of heat transfer catheter 100, while intermediate sections of flexible conduit 104 allow heat transfer catheter 100 to bend to adapt to the patient's particular anatomy. The dimensions of oval nodes 102 are not critical, and can change depending upon the subject in which heat transfer catheter 100 is to be placed so as to best adapt to the specific anatomy of that subject, although the cross-section of each node 102 should have a major axis that is larger than a perpendicular minor axis.

Oval shaped, hollow nodes 102 and sections of flexible conduit 104 may be formed of any suitable, biologically compatible material, such as latex, silicone, TEFLON, or any other biologically inert materials that will allow heat transfer between the inside of heat transfer catheter 100 and the patient's body in which heat transfer catheter 100 is placed. In order to provide nodes with greater rigidity than interconnecting sections of flexible conduit 104, as shown in the close-up sectional view of a portion of heat transfer catheter 100 of FIG. 3, nodes 102 may (by way of non-limiting example) be formed of the same material as conduit 104, but may have a thickness significantly greater than flexible conduit 104, thus providing nodes 102 with greater rigidity than conduit 104. Alternatively, nodes 102 may be formed of a different biologically inert material having greater rigidity than conduit 104, or of the same material but with reinforcement that increases the rigidity of nodes 102 beyond that of flexible conduit 104. In a particularly preferred configuration, nodes 102 may be positioned approximately 1-10 millimeters apart from one another so as to optimally adapt to typical colon structures. However, the size, shape and number of nodes 102 and sections of flexible conduit 104 may be readily adjusted to best fit the colon or other anatomical structures of a given patient (human, animal, multicellular organism, etc.).

With this configuration of nodes 102 having greater rigidity than intermediate sections of flexible conduit 104, heat transfer catheter 100 may be more easily placed into difficult-to-navigate areas of a patient's body, such as by way of non-limiting example a patient's colon, and more particularly may more easily pass the turning areas in the sigmoid, ascending, transverse, and descending colon, all while maintaining the overall length of heat transfer catheter 100 so as to avoid it being propelled backward by pressure or bowel movements.

Moreover, while the above exemplary discussion focuses on use of the heat transfer catheter 100 for rectal colon heat transfer, heat transfer catheter 100 may likewise be used in other areas of the patient's body, such as (by way of non-limiting example) for upper body cavity cooling, in which the heat transfer catheter 100 is placed in the patient's esophagus, stomach, or upper digestive tract, with heat transfer being carried out at such location to better focus heating or cooling where specifically needed for a given patient condition.

The heat transfer fluid carried through heat transfer catheter 100 may comprise any material or combination of different materials, either fluid, oil, or viscous, including but not limited to water, a physiological fluid such as Ringer's solution, a chemical fluid, a solvent, a biological fluid, a therapeutic fluid, a lubricant, and combinations of the foregoing or similarly configured fluids. As explained above, heat transfer inlet line 110 and heat transfer outlet line 112 are connected to temperature-controlling apparatus of fluid control unit 200 to enable the circulation of the fluid from the temperature-controlling apparatus to heat transfer fluid inlet line 110, through the length of heat transfer catheter 100 from its proximal end 101(a) to its distal end 101(b), and further through the interior of heat transfer catheter 100 from its distal end 101(b) to its proximal end 101(a) (outside of heat transfer fluid inlet line 110), further to heat transfer fluid outlet line 112 and then back to the temperature-controlling apparatus. The temperature exchange fluid may be driven either via pump 202 or any other fluid handling device, such as (by way of non-limiting example) a syringe, to circulate the fluid or mix of different fluids. Arrows on FIGS. 2 and 3 show the flow path of fluids through their respective flow paths in heat transfer catheter 100, including fluid line 116 receiving heat transfer fluid from heat transfer inlet line 110 and directing it toward the distal end of heat transfer catheter 100. The heat transfer fluid may be driven continuously.

Irrigation line 114 may extend the full length of heat transfer catheter 100, and may include an irrigation line outlet 115 that may have an oval shaped structure. As is the case with heat transfer fluid inlet line 110, irrigation line 114 may extend through the interior of nodes 102 and sections of flexible conduit 104, extending essentially parallel to heat transfer fluid inlet line 110. The function of irrigation line 114 is to perform lubrication, enema, or to remove the contents from the patient's colon rectum lumen. Irrigation fluid may be injected or withdrawn via the inlet through the span of irrigation line 114 and further to the outlet 115, thereby irrigating the materials in the patient's colon. As explained above, the irrigation fluid may be driven either via a pump in irrigation unit 214, or via a device such as a syringe to perform the irrigation or lubrication function. The irrigation fluid may be made of any materials or any combination of different materials, either fluid, oil, or viscous, including but not limited to water, a physiological fluid such as Ringer's solution, a chemical fluid, a solvent, a biological fluid, a therapeutic fluid, lubricant or a combination of the above.

Optionally, and with continued reference to FIG. 2, an endoscopic camera 220 may also be provided attaching to and optionally extending through and out of the distal end 101(b) of heat transfer catheter 100, the proximal end of camera 220 connecting to a video screen 222 to aid the clinician in properly placing heat transfer catheter 100 at the desired location within the patient by visualizing the body cavity (e.g., the patient's intestine) in which the heat transfer catheter 100 is being placed.

Figure 4:
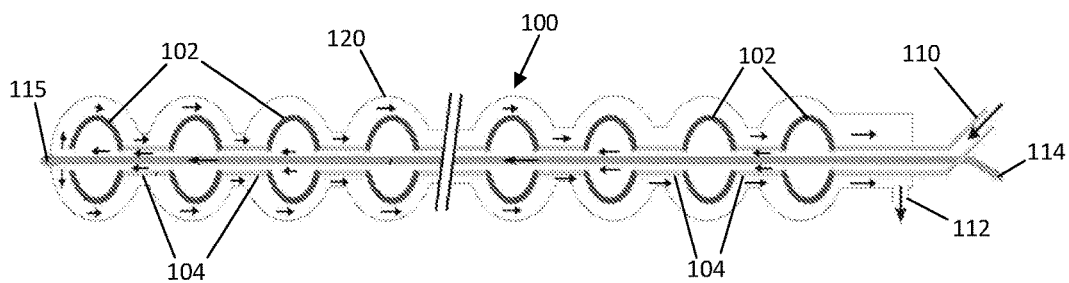
FIG. 4 shows a cross-sectional view of a heat transfer catheter for use in the system of FIG. 2 in accordance with further aspects of an embodiment of the invention.
Figure 4A:
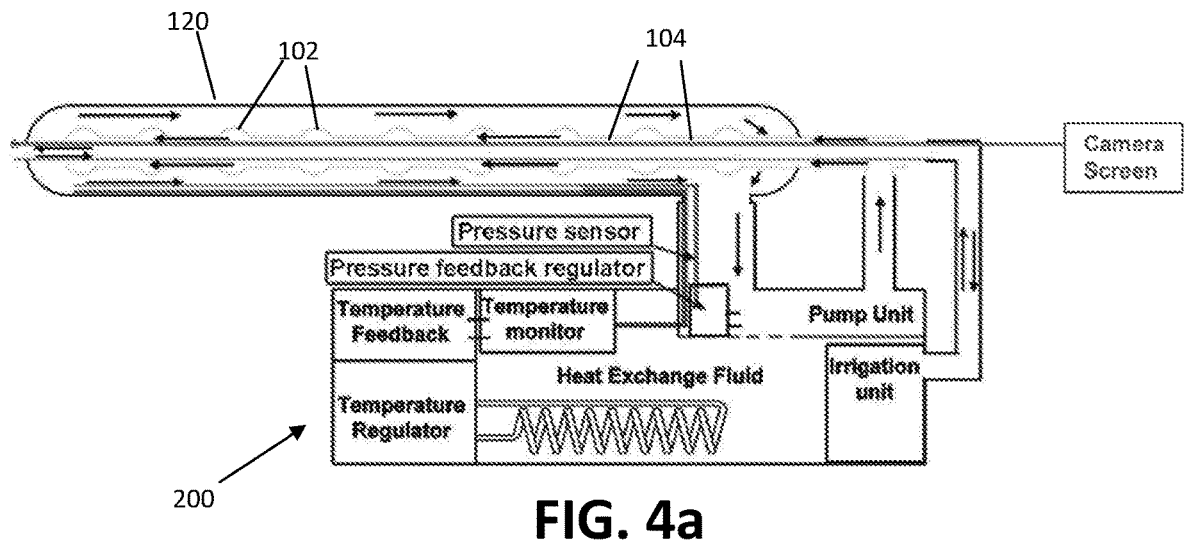
FIG. 4a shows a schematic view of the heat transfer catheter of FIG. 4 in communication with a fluid control unit and a camera.

Referring next to FIG. 4 (fluid control unit 200 omitted for clarity), heat transfer catheter 100 may also include an inflatable, flexible or elastic balloon-shaped membranous tube 120. If such a balloon 100 is provided, heat transfer fluid inlet line 110 leads directly and attaches to the proximal-most section of flexible conduit 104, thus carrying the heat transfer fluid delivered to the proximal end of heat transfer catheter 100 toward the distal end of heat transfer catheter 100 through the interiors of nodes 102 and sections of flexible conduit 104. At the distal end of heat transfer catheter 100, the heat transfer fluid exits the distal-most node 102, and thereafter flows from the distal end of heat transfer catheter 100 to the proximal end of heat transfer catheter 100 between the exterior of nodes 102 and sections of flexible conduit 104, and the interior of balloon 120. At the proximal end of heat transfer catheter 100, the heat transfer fluid exits from balloon 120 through heat transfer fluid outlet line 112. The directional arrows on FIG. 4 show the direction of fluid flows through heat transfer catheter 100. FIG. 4a provides a schematic view of the heat transfer catheter 100 shown in FIG. 4 in combination with fluid control unit 200 configured as described above.

Balloon 120 should be sufficiently thin so as to ensure efficient heat transfer between heat transfer catheter 100 and the patient's tissue, but it is likewise important to ensure that balloon 120 is of sufficient strength so as to protect against breakage or rupture and thus potential damage to the patient's tissue. Thus, balloon 120 may be formed of more than one layer of thin membrane material to help protect against potential leakage while maintaining efficient heat transfer.

Once again, irrigation line 114 is provided, extending from the proximal end of heat transfer catheter 100 to and through the distal end thereof so as to provide irrigation fluid from its tip 115 to the patient's colon (or other such anatomy in which heat transfer catheter 100 is placed).

Figure 5:
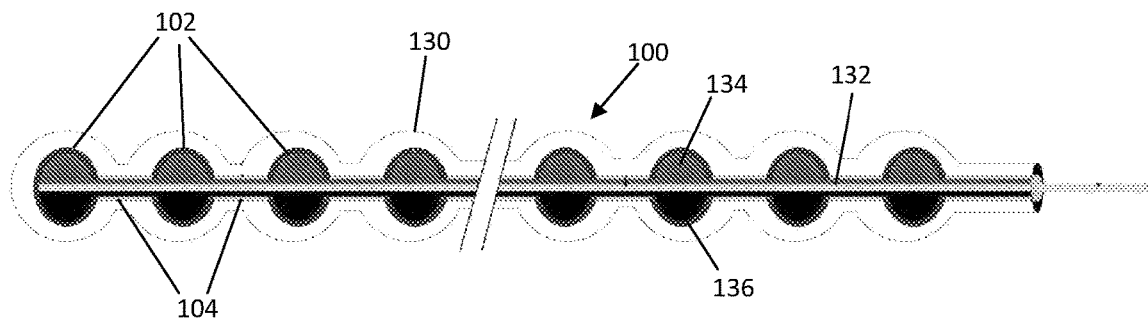
FIG. 5 shows a cross-sectional view of a heat transfer catheter in accordance with further aspects of an embodiment of the invention.

Next, according to further aspects of an embodiment of the invention and with reference to FIG. 5, heat transfer catheter 100 may be equipped to contain an endothermic or exothermic reaction to effect heat transfer, instead of receiving a heat transfer fluid from fluid control unit 200. As used herein, the term "endothermic process" refers to a process or reaction in which the system absorbs energy (e.g., absorption of heat from the surroundings), and the term "exothermic process" refers to a process or reaction in which the system releases energy (e.g., in the form of heat). In order to contain such processes, nodes 102 and sections of flexible conduit 104 configured as described above form a sealed compartment containing reactants (as discussed further below), and are optionally contained within a closed external membrane 130 formed of flexible material, such as the balloon 120 of FIG. 4, with such closed external membrane 130 serving to prevent leakage of materials from nodes 102 and flexible conduit sections 104. In this configuration, the heat transfer fluid carrier is thus defined by nodes 102 and flexible conduit sections 104. Such heat transfer fluid carrier is separated into two or more compartments by one or more separating membranes 132. Those separate compartments contain different materials, such as a first reactant 134 and a second reactant 136 that, when combined or in contact with one another, carry out an endothermic or exothermic reaction.

Reactants 134 and 136 may comprise different endothermic or exothermic materials or any combination of different materials in either powder, particle, solid, fluid, oil, or viscous form. An example of a suitable configuration for use with the invention to allow an endothermic reaction include selecting [Ba(OH)2 8H2O] as reactant 134, and [(NH4)(NO3)] as reactant 136, although those skilled in the art will recognize that various endothermic reactions (and corresponding materials) are currently available and may be used without departing from the spirit and scope of the invention. Likewise, an example of a suitable configuration for use with the invention to allow an exothermic reaction include selecting a small amount of notched ferrous metal as reactant 134 and a supersaturated solution of sodium acetate (3H2 CH3COONa) in water as reactant 136, although those skilled in the art will recognize that various exothermic reactants (and corresponding materials) are currently available and may be used without departing from the spirit and scope of the invention.

The separating membrane 132 is removable or breakable at the time that the endothermic or exothermic reaction is desired to be carried out, such that reactants 134 and 136 will mix with one another within the heat transfer fluid carrier. Separating membrane 132 may be made of either strong or fragile materials which may be readily selected by those of ordinary skill in the art. If the separating membrane 132 is made of strong materials, then the separating membrane 132 may be pulled to cause the mixing of reactants 134 and 136. If the separating membrane 132 is made of fragile materials, then the separating membrane 132 may be broken by squeezing the heat transfer fluid carrier, thereby causing the mixing of reactants 134 and 136. The orientation of separating membrane 132 may be at any plane in the interior of the heat transfer fluid carrier. Optionally, separating membrane 132 may also comprise a small bag or other container holding a small amount of one of reactants 134 or 136, with the remaining reactant held within the rest of the internal space of the heat transfer fluid carrier.

As used herein, the term "heat transfer fluid" is intended to include the reactants 134 and 136 shown in FIG. 5.

Next, and in accordance with an alternative embodiment of the invention (fluid control unit 200 being omitted for clarity), a cylindrical heat transfer catheter may be provided of sufficient rigidity so as to allow its placement within the colon of a patient while enabling its navigation through the turns of the patient's sigmoid, ascending, transverse, and descending colon. In this configuration, heat transfer fluid inlet line 110 extends from the proximal end of heat transfer catheter 100 to the distal end thereof, and while round, otherwise has a wall configuration identical to that described above for nodes 102 so as to provide fluid inlet line 110 with sufficient rigidity to allow its navigation through the patient's body to its intended location. The distal end of heat transfer fluid inlet line 110 opens to the interior of cylindrical balloon 120, directing the heat transfer fluid from heat transfer fluid inlet line 110 to the interior of cylindrical balloon 120, and back to the proximal end of heat transfer catheter 100, where the heat transfer fluid again exits through heat transfer fluid outlet line 112. Irrigation line 114 may again be provided, extending through heat transfer fluid inlet line 110 and exiting cylindrical balloon 120 in the same manner as described above. The directional arrows on FIG. 6 show the fluid flows through heat transfer catheter 100.

Figure 6:
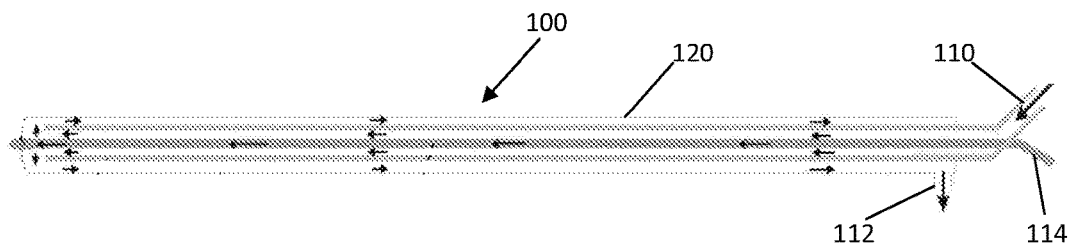
FIG. 6 shows a cross-sectional view of a heat transfer catheter for use in the system of FIG. 2 in accordance with still further aspects of an embodiment of the invention.

With continued reference to the embodiment reflected in FIG. 6, cylindrical balloon 120 is preferably formed with a rounded, smooth distal tip so as to aid in its insertion into the patient's body.

The devices and methods disclosed above may be used to perform temperature management in the entirety or a portion of an organism or a human body, to perform various therapies and to attain various purposes such as cell protection. The body temperature management devices and methods disclosed herein may be used by inserting such devices into, for example, the colon of a patient or an animal in order to perform temperature management of the person or animal.

While the exemplary embodiments have been shown and described, it will be understood by those skilled in the art that various changes in form and details may be made thereto without departing from the spirit and scope of the present disclosure as defined by the appended claims.

In addition, many modifications can be made to adapt a particular situation or material to the teachings of the present disclosure without departing from the essential scope thereof. Therefore, it is intended that the present disclosure not be limited to the particular exemplary embodiments disclosed as the best mode contemplated for carrying out the present disclosure, but that the present disclosure will include all embodiments falling within the scope of the appended claims.

What is claimed is:

1. A heat transfer catheter system comprising:
a heat transfer catheter, said heat transfer catheter further comprising:
a plurality of hollow nodes, wherein each hollow nodes of said plurality of hollow nodes comprises a discrete, hollow oval-shaped container that is circumferentially aligned about said heat transfer catheter and incrementally spaced along said heat transfer catheter;
a flexible conduit attaching adjacent hollow nodes and allowing fluid communication between said adjacent hollow nodes and said flexible conduit, wherein said flexible conduit has greater flexibility than said hollow nodes, and wherein an interior of said hollow nodes and an interior of said flexible conduit provide a heat transfer fluid carrier; and
a heat transfer fluid within said heat transfer fluid carrier.

2. The heat transfer catheter system of claim 1, further comprising a heat transfer fluid inlet line extending through said flexible conduit and said plurality of hollow nodes, said heat transfer fluid inlet line having a distal end opening into an interior of said heat transfer fluid carrier.

3. The heat transfer catheter system of claim 2, further comprising a heat transfer fluid outlet line in fluid communication with said interior of said heat transfer fluid carrier.

4. The heat transfer catheter system of claim 3, further comprising a fluid control unit, wherein said heat transfer fluid inlet line and said heat transfer fluid outlet line are in fluid communication with said fluid control unit to define a recirculating heat transfer fluid circuit.

5. The heat transfer catheter system of claim 1, further comprising a temperature sensor within said heat transfer fluid carrier.

6. The heat transfer catheter system of claim 1, further comprising a pressure sensor within said heat transfer fluid carrier.

7. The heat transfer catheter system of claim 1, further comprising an endoscopic camera attached to said heat transfer catheter.

8. The heat transfer catheter system of claim 1, wherein said heat transfer fluid carrier is contained within an inflatable balloon.

9. The heat transfer catheter system of claim 8, further comprising a heat transfer fluid outlet line in fluid communication with an interior of said inflatable balloon.

10. The heat transfer catheter system of claim 9, further comprising:
a heat transfer fluid inlet line connected to a proximal end of said heat transfer fluid carrier; and
a fluid control unit, wherein said heat transfer fluid inlet line and said heat transfer fluid outline line are in fluid communication with said fluid control unit to define a recirculating heat transfer fluid circuit.

11. The heat transfer catheter system of claim 8, wherein a distal end of said heat transfer fluid carrier opens to an interior, distal end of said balloon.

12. The heat transfer catheter of claim 1, further comprising a membrane extending through said heat transfer fluid carrier, wherein said heat transfer fluid further comprises a first reactant and a second reactant, and wherein said membrane separates said first reactant from said second reactant.

13. The heat transfer catheter of claim 12, wherein said membrane is removable from said heat transfer fluid carrier, and wherein said heat transfer catheter is configured to cause mixing of said first reactant with said second reactant upon removal of said membrane from said heat transfer fluid carrier.

14. The heat transfer catheter of claim 1, further comprising an irrigation line extending through said heat transfer catheter and exiting through a distal end of said heat transfer catheter.

15. A method for body temperature management, comprising:
providing a heat transfer catheter, said heat transfer catheter further comprising:
a plurality of hollow nodes, wherein each hollow nodes of said plurality of hollow nodes comprises a discrete, hollow oval-shaped container that is circumferentially aligned about said heat transfer catheter and incrementally spaced along said heat transfer catheter; and a flexible conduit attaching adjacent hollow nodes and allowing fluid communication between said adjacent hollow nodes and said flexible conduit, wherein said flexible conduit has greater flexibility than said hollow nodes, and wherein an interior of said hollow nodes and an interior of said flexible conduit provide a heat transfer fluid carrier;

inserting said heat transfer catheter into a body cavity of a patient; and causing a heat transfer fluid in said heat transfer fluid carrier to effect heat transfer between said heat transfer fluid carrier and tissue in the body cavity of the patient.

16. The method for body temperature management of claim 15, said heat transfer catheter further comprising an irrigation line extending through said heat transfer catheter, the method further comprising the step of directing an irrigation fluid to the body cavity of the patient through said irrigation line.

* * * * *